(12) United States Patent
Huff et al.

(10) Patent No.: US 9,442,101 B2
(45) Date of Patent: Sep. 13, 2016

(54) SYSTEM FOR DETERMINING BIOFUEL CONCENTRATION

(71) Applicant: UT-Battelle LLC, Oak Ridge, TN (US)

(72) Inventors: Shean P. Huff, Knoxville, TN (US); Christopher James Janke, Oliver Springs, TN (US); Michael D. Kass, Oak Ridge, TN (US); Samuel Arthur Lewis, Sr., Andersonville, TN (US); Steven J. Pawel, Oak Ridge, TN (US); Timothy J. Theiss, Kingston, TN (US)

(73) Assignee: UT-Battelle, LLC, Oak Ridge, TN (US)

( * ) Notice: Subject to any disclaimer, the term of this patent is extended or adjusted under 35 U.S.C. 154(b) by 382 days.

(21) Appl. No.: 13/939,479

(22) Filed: Jul. 11, 2013

(65) Prior Publication Data
US 2015/0017065 A1    Jan. 15, 2015

(51) Int. Cl.
*G01N 35/00* (2006.01)
*G01N 33/28* (2006.01)

(52) U.S. Cl.
CPC .................................. *G01N 33/2852* (2013.01)

(58) Field of Classification Search
CPC .................. G01M 3/17; G01M 3/006; G01N 2030/8854; G01N 33/22; G01N 33/225; G01N 27/12

USPC .......................................................... 422/404
See application file for complete search history.

(56) References Cited

U.S. PATENT DOCUMENTS

| | | | | |
|---|---|---|---|---|
| 4,631,952 A | * | 12/1986 | Donaghey | G01M 3/045 338/34 |
| 4,855,706 A | | 8/1989 | Hauptly | |
| 5,256,574 A | | 10/1993 | Neuburger et al. | |
| 7,461,560 B2 | | 12/2008 | Arms et al. | |
| 2011/0053283 A1 | * | 3/2011 | Hood | G01N 33/14 436/104 |
| 2011/0113893 A1 | | 5/2011 | Arms et al. | |

FOREIGN PATENT DOCUMENTS

| | | |
|---|---|---|
| CN | 101614522 | 12/2009 |
| JP | 2003-121343 | 4/2003 |
| JP | 2011-209255 | 10/2011 |

* cited by examiner

*Primary Examiner* — Jill Warden
*Assistant Examiner* — Brittany Fisher
(74) *Attorney, Agent, or Firm* — Warner Norcross & Judd LLP

(57) ABSTRACT

A measurement device or system configured to measure the content of biofuels within a fuel blend. By measuring a state of a responsive material within a fuel blend, a biofuel content of the fuel blend may be measured. For example, the solubility of a responsive material to biofuel content within a fuel blend, may affect a property of the responsive material, such as shape, dimensional size, or electrical impedance, which may be measured and used as a basis for determining biofuel content.

20 Claims, 2 Drawing Sheets

SYSTEM FOR DETERMINING BIOFUEL CONCENTRATION

This invention was made with government support under Contract No. DE-AC05-00OR22725 awarded by the U.S. Department of Energy. The government has certain rights in the invention.

BACKGROUND OF THE INVENTION

The present invention relates to determining biofuel concentration, and more specifically to determining biofuel concentration in petroleum-derived fuels.

Biofuels are being added more frequently to petroleum-derived fuels (also known as petrofuels), often times to supplement the more scarce or costly petrofuels. This type of fuel mixture is called a fuel blend, and may include a variety of fuels, such as biofuel, petrofuel, or any other fuel, or a combination thereof. One such fuel blend includes a low level of ethanol, a type of biofuel, and is referred to as E10. Another example of a fuel blend containing ethanol is called E15 and another example is called E85. And, yet another example of a fuel blend includes biodiesel, another type of biofuel.

Although biofuels have made their way into the market, some conventional engine systems are incompatible with fuel blends including biofuels. An incompatible system may be reconfigured for compatibility, but often times, this conversion process is expensive and labor intensive. Examples of biofuel incompatible systems still in use today include small engines used in lawnmowers, snowblowers, chainsaws, trimmers and other applications. Other example engine systems are included in small outdoor power equipment, recreational vehicles, off-road or farming equipment, and marine and aviation applications. Due to these compatibility issues, a consumer in possession of an engine system incompatible with biofuel may be motivated to obtain fuel that does not contain biofuels, such as ethanol. An ethanol free source may be difficult to locate, and there may be no guarantee that fuel advertised as 100% gasoline does in fact contain no ethanol by its outward appearance.

Some conventional engine systems may be compatible with biofuels, but because biofuels and petrofuels may exhibit different combustion properties, these conventional engine systems may adapt to operate as a function of biofuel content. In some cases, the system may be optimized based on biofuel content. One conventional engine system that has been configured to be biofuel compatible is the combustion engine powering many vehicles on the road, today. Other example engine systems that may be configured for biofuel compatibility include those mentioned above in connection with incompatible systems. These conventional engine systems may measure biofuel concentration in a fuel blend by utilizing a conventional sensor, also referred to as a flex fuel sensor. By measuring the biofuel concentration of the fuel blend, the system may adapt or calibrate itself for operation. But, these conventional flex fuel sensors are considered by many to be expensive, unreliable, and inefficient energy consumers. They may also be highly sensitive to contaminants, particularly to water, prevalent in many fuel blends.

For alcohol-gasoline fuel blends, such as ethanol-gasoline blends, two types of fuel composition sensors or conventional flex fuel sensors are often times used. The first type is an optical-based sensor that measures the refractive index, and the second type is a dielectric sensor that measures the dielectric constant of the field. Of these two types, the dielectric sensor is the most widely used. Both types, however, have two primary downsides: they are in many cases expensive to manufacture and maintain, and they may be highly sensitive to fuel contaminants, particularly water.

In contrast to petrofuels, such as gasoline or diesel, biofuels are often highly polar. The degree of fluid polarity may impact the electrical current produced in a dielectric sensor. For example, an increased polarity may cause an increase in the measured electrical current. Contaminants, particularly water, are also often highly polar, and may provide additional current contributions in the dielectric sensor that may not be distinguishable from the biofuel contribution. Thus, accurate measurements may not be obtainable using a dielectric sensor unless fuel contamination is low or below a threshold.

The refractive index (or optical) sensor may also be impacted by contaminants, such as water. This sensor technique may be less sensitive to contaminants than the dielectric method, but it is considered by many to be more complex in structure, and therefore more expensive. Additionally, optical sensors may utilize windows, such as a transparent or translucent material, through which to transmit a signal. These windows may become dirty such that maintenance and replacement are frequent considerations.

SUMMARY OF THE INVENTION

The present invention provides a measuring device capable of determining a content of biofuel within a fuel blend. The measuring device may include a responsive material, such as silicone rubber, that may expand or contract (or both) in the presence of biofuel, and an indicator that provides information relating to the concentration of biofuel based the responsive material. The indicator may include a gauge or a visual indicator, or may be an output of a sensor that measures the one or more properties of the responsive material.

For instance, in embodiments with a sensor, the sensor may directly or indirectly measure a linear dimension of the responsive material, such as thickness or length, or a volume of the responsive material. The sensor may include one or more sensor types, including a linear transducer, an optical sensor, a rheostat based sensor, and a pressure sensor. An example indirect measurement of a property of the responsive material includes containing the responsive material in a restricted space, and utilizing a pressure sensor to detect swelling of the responsive material in that space in response to changes in biofuel concentration. In another example, a rheostat based sensor may detect electrical properties of the responsive material indicative of a dimension or volume of the responsive material.

The responsive material may be capable of changing dimensionally in response to changes in the concentration of biofuel within a fuel blend. The responsive material may be soluble to the biofuel but insoluble to other components of the fuel blend, including at least one of contaminants and additives. For example, one type of contaminant, water, may be insoluble with respect to the responsive material such that the information relating to the concentration of biofuel is unaffected by changes in water content within the fuel blend.

In one aspect, a measuring device including a responsive material capable of changing dimensionally based on biofuel content may provide a low-cost and simple system for accurately detecting presence or concentration of biofuel in a fuel. For example, the measuring device may utilize the property of the responsive material, such as silicone rubber, with respect to biofuel to determine information relating to the concentration of biofuel in the fuel blend. The shape or size of the responsive material may change due to absorption of the biofuel. In other words, the solubility of the responsive material to biofuel content within the fuel blend may affect a property of the responsive material, such as shape, dimensional size, or electrical impedance. The measuring device may measure these properties, directly or indirectly, to use them as a basis for determining biofuel content.

These and other objects, advantages, and features of the invention will be more fully understood and appreciated by reference to the description of the current embodiment and the drawings.

Before the embodiments of the invention are explained in detail, it is to be understood that the invention is not limited to the details of operation or to the details of construction and the arrangement of the components set forth in the following description or illustrated in the drawings. The invention may be implemented in various other embodiments and of being practiced or being carried out in alternative ways not expressly disclosed herein. Also, it is to be understood that the phraseology and terminology used herein are for the purpose of description and should not be regarded as limiting. The use of "including" and "comprising" and variations thereof is meant to encompass the items listed thereafter and equivalents thereof as well as additional items and equivalents thereof. Further, enumeration may be used in the description of various embodiments. Unless otherwise expressly stated, the use of enumeration should not be construed as limiting the invention to any specific order or number of components. Nor should the use of enumeration be construed as excluding from the scope of the invention any additional steps or components that might be combined with or into the enumerated steps or components.

Directional terms, such as "vertical," "horizontal," "top," "bottom," "upper," "lower," "inner," "inwardly," "outer" and "outwardly," are used to assist in describing the invention based on the orientation of the embodiments shown in the illustrations. The use of directional terms should not be interpreted to limit the invention to any specific orientation(s).

DESCRIPTION OF THE CURRENT EMBODIMENT

The present application discloses multiple embodiments of a measurement device or system configured to measure the content of biofuels within a fuel blend. More specifically, many of the embodiments described herein contemplate utilizing a property of a responsive material in contact with or within a fuel blend to determine biofuel content of the fuel blend. For example, the shape or size of the responsive material may change due to absorption of biofuel. The solubility of the responsive material to biofuel content within a fuel blend may affect a property of the responsive material, such as shape, dimensional size, or electrical impedance, which may be measured and used as a basis for determining biofuel content. Although embodiments are described with a particular configuration of features and components, it should be understood that none of the disclosed features and components is exclusive to one embodiment. The features and components described with respect to one embodiment may be included in another embodiment, and may be interchanged with another feature or component described herein.

A. First Embodiment

Figure 1:
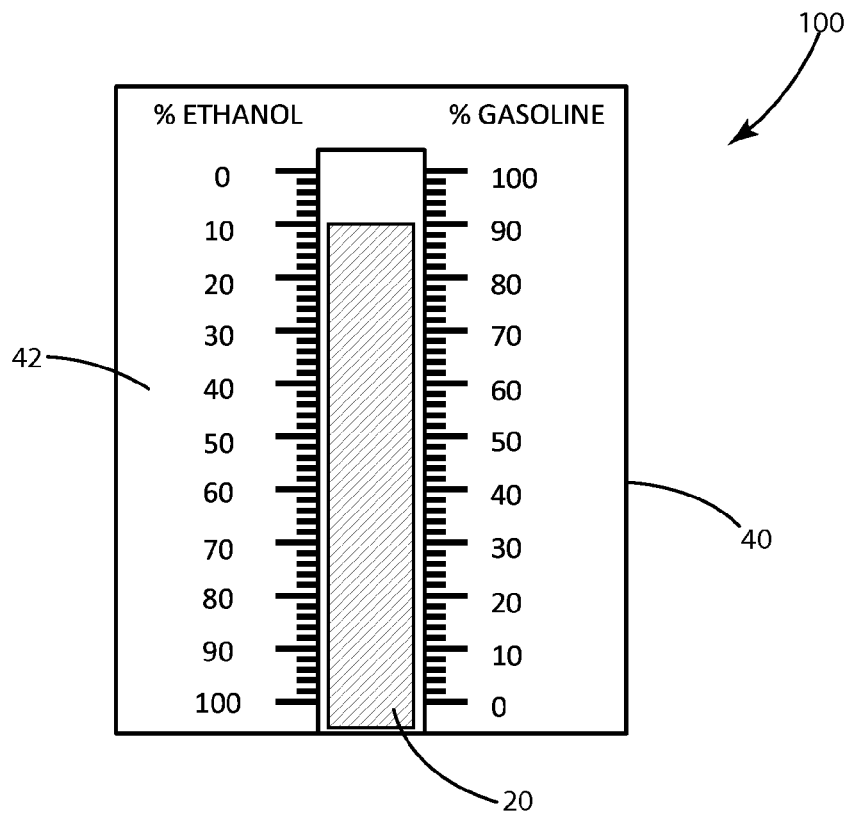
FIG. 1 shows a representative view of a sensor in accordance with one embodiment.

A measurement device in accordance with one embodiment is shown in FIG. 1 and designated 100. The measurement device 100 may include a responsive material 20 configured to aid in measuring a biofuel concentration of a fuel blend. The responsive material 20 may change dimensionally in proportion to changes in biofuel concentration. For example, the responsive material 20 may increase in volume or swell as the percentage of biofuel within a fuel blend decreases. By knowing the relationship between the concentration of biofuel within a fuel blend and a dimensional property of the responsive material 20, the concentration of biofuel may be determined by directly or indirectly measuring a dimensional property of the responsive material 20.

Figure 2:
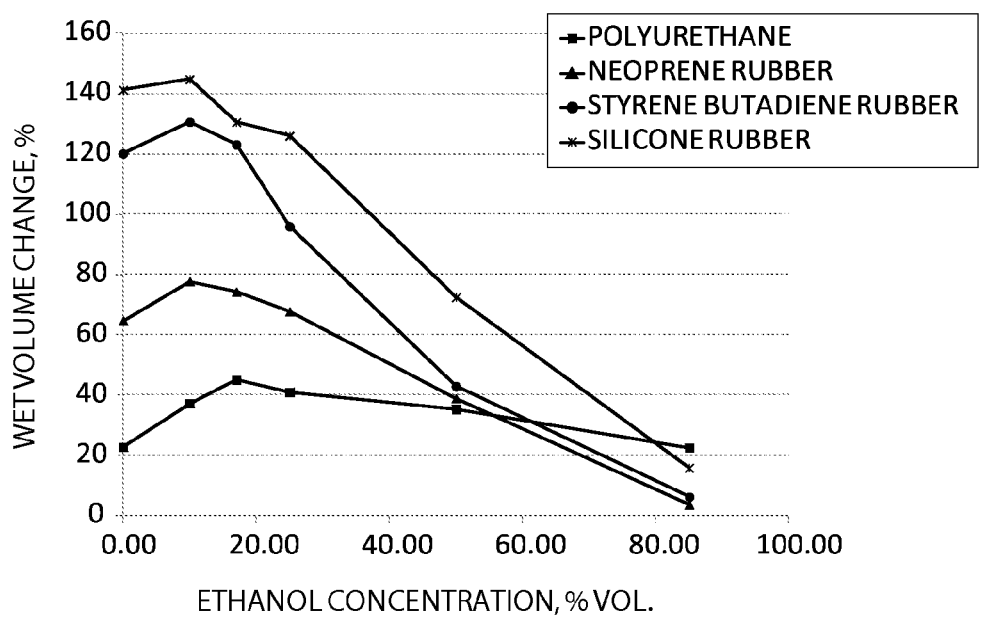
FIG. 2 is a plot showing a relationship between volume and biofuel concentration for various materials in accordance with one embodiment.

For example, the plot in FIG. 2 shows an experimentally determined relationship between ethanol content in gasoline and volume for a variety of responsive materials, including polyurethane, neoprene rubber, styrene butadiene rubber, and silicone rubber. It should be understood that the present application is not limited to these materials, and that other materials that change in proportion to changes in biofuel concentration are contemplated including other types of rubber. As can be seen in FIG. 2, silicone rubber exhibits a near linear dimensional relationship between 10% (E10) and 85% (E85) ethanol by volume in gasoline. The volume change in the silicone rubber was experimentally found to be reversible, meaning the material may return to its original volume after drying without substantial structural degradation. It can also be seen that the other materials, polyurethane, neoprene rubber, and styrene butadiene rubber, change in proportion to ethanol concentration in gasoline.

In contrast to conventional flex fuel sensors, a responsive material 20 according to one embodiment, such as a solubility-based silicone rubber, may be less expensive and less sensitive to additives or contaminants, particularly water. The responsive material 20 may be soluble to biofuel but insoluble to contaminants or additives in a fuel blend. For example, solubility, or volume swell, of silicone rubber as identified in FIG. 2 is sensitive to biofuel concentration within a fuel blend, such as an ethanol-gasoline blend. However, because additives or contaminants, such as water, may be in large part insoluble to silicone, the silicone rubber, while being sensitive to biofuel concentration, may remain unaffected by the presence of contaminants in the fuel blend. By utilizing a responsive material 20, such as silicone rubber, the measuring device 100 may be configured to determine biofuel concentration without being significantly affected by presence of additives or contaminants.

In the illustrated embodiment of FIG. 1, the measuring device 100 may include a gauge 40, on or within which the responsive material 20 may be disposed. As an example, the gauge 40 may be an unsealed vial containing the responsive material 20. The gauge 40 along with the responsive material 20 may be placed in a fuel blend or allow a fuel blend to be poured into the gauge 40. The gauge 40 may be formed of one or more materials capable of withstanding contact with various fuel blends without substantially degrading. Glass and fuel resistant plastics are some examples of such materials.

In an alternative embodiment, the responsive material 20 may be completely exposed on or within the gauge 40. For instance, the gauge 40 may be a fuel resistant plastic, and may be secured to the responsive material 20 such that the responsive material 20 is exposed but capable of changing dimensionally in response to contact with a biofuel. An end of the responsive material 20 may be fixedly secured to the gauge 40, while other portions of the responsive material 20, distal from the end, may be secured to the gauge 40 in a manner that allows dimensional changes in the responsive material 20. As an example, the gauge 40 may include one or more apertures that guide and enable the responsive material 20 to change in volume such that a measurement or determination of biofuel content can be obtained using the measuring device 100.

By disposing the responsive material 20 within or in contact with a fuel blend, the responsive material 20 may indicate a concentration of biofuel. For example, a dimensional property of the responsive material 20, such as thickness, may indicate a biofuel concentration. The initial size and dimensions of the responsive material 20 used in the measuring device 100 may vary depending on a variety of factors, including, for example, a desired response time to changes in biofuel concentration. For instance, faster response times may be achieved by using a thinner responsive material 20 along with a smaller and thinner gauge 40. Faster response times may also be achieved by increasing the amount of surface area of the responsive material 24 that is exposed to the fuel blend. For example, a thin coating of responsive material 24, such as silicon, may provide a more rapid response relative to a larger sized responsive material 24.

The measuring device 100 may utilize the volume swell of the responsive material 20 as a basis for determining the biofuel concentration, in a manner similar to a thermometer. For example, the gauge 40 may include a scale 42 calibrated against a known relationship between volume swell of the responsive material 20 and an ethanol or gasoline concentration. As depicted, the responsive material 20 indicates an ethanol concentration of approximately 10% (E10) and a gasoline concentration of 90%. In the illustrated embodiment, the lowest reading corresponding to a smaller dimensional size of the responsive material 20 is 100% ethanol, and the highest reading corresponding to a larger dimensional size is 0% ethanol. The measuring device 100 may be used for both end consumer use and for gas station owners so that either may effectively measure biofuel content, such as the concentration of ethanol in a gasoline tank.

B. Second Embodiment

Figure 3:
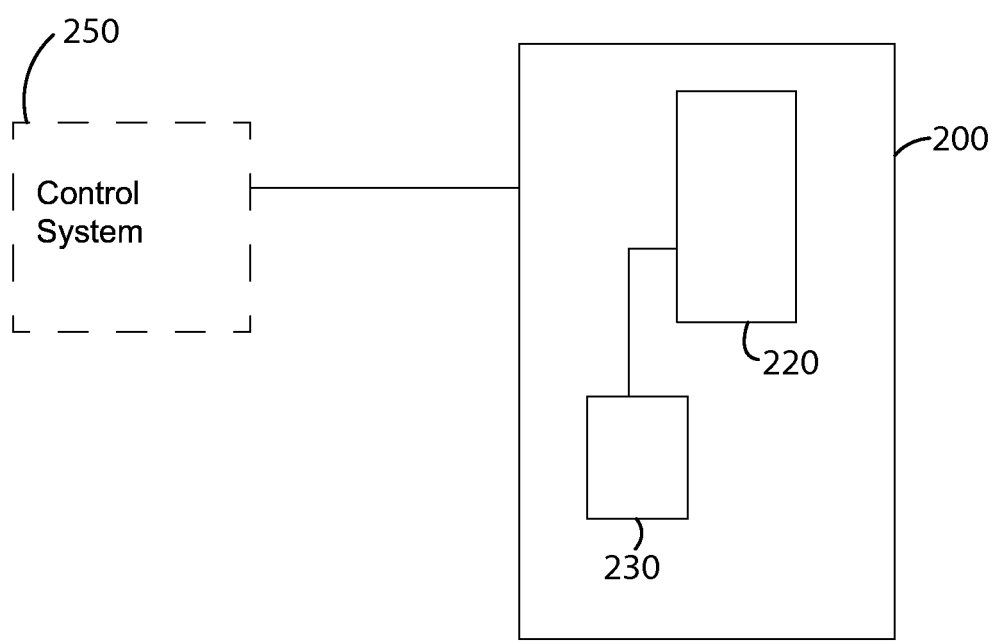
FIG. 3 shows a representative view of a sensor in accordance with one embodiment.

Turning now to FIG. 3, a measurement device in accordance with another embodiment is shown, and designated 200. The measuring device 200 may be similar to the measuring device 100 but with several exceptions. The measuring device 200 may include a responsive material 220 similar to the responsive material 20 described with respect to the illustrated embodiment of FIG. 1. For example, the responsive material 220 may be formed of silicone rubber configured to change in proportion to changes in biofuel concentration, such as by changing dimensionally in response to changes in biofuel concentration.

The measuring device 200 may also include a sensor 230 configured to provide an output based on one or more properties of the responsive material 220, which may be sensed directly or indirectly. Because these properties may be proportional to the biofuel concentration, measurements conducted by the sensor 230 may be used as a basis for providing an output corresponding to the biofuel concentration. For instance, the sensor 230 may include circuitry capable of outputting a voltage in a range, such as 0-10V, that correlates to a 0-100% range of biofuel concentration. 10 V may represent 100% biofuel concentration, while 0 V may be indicative of 0% biofuel concentration. Alternatively, rather than an analog voltage output representative of biofuel concentration, the output from the sensor 230 may be a visual output indicative of biofuel concentration. As an example, the output may be a dial or an LCD display that identifies biofuel concentration to an observer.

The sensor 230 may utilize a variety of sensing or measuring techniques to determine biofuel concentration based on properties of the responsive material 220. For example, dimensional or electrical properties of the responsive material 220 in the presence of a fuel blend may be measured directly or indirectly.

In one embodiment, the sensor 230 may include a strain gage affixed to the responsive material 220. An electrical resistance of the strain gauge may change in proportion to a change in a dimensional property of the responsive material, such as its volume. The sensor 230 may be calibrated to the electrical resistance of the strain gauge in order to provide an output corresponding to biofuel concentration. In other words, the sensor 230 may utilize the strain gauge to detect a volume of the responsive material 220, and, based on this detected volume, may provide an output indicative of biofuel concentration.

In another embodiment, the measuring device 200 may include a cell containing the responsive material 220 such that the responsive material 220 is contained within a restricted space defined by the cell. Expansion and contraction of the responsive material 220 may result in pressure changes within this restricted space. The sensor 230 may be configured to measure pressure of the cell, and therefore may indirectly measure a dimensional property of the responsive material 220. By calibrating the measuring device 200 to pressure and biofuel content for a fuel blend, the measuring device 200 may determine biofuel content based on a measured pressure.

In yet another embodiment, the sensor 230 may measure linear expansion of the responsive material 220, similar in some respects to the embodiment described with respect to FIG. 1, to determine biofuel concentration. As an example, the sensor 230 may be calibrated to determine biofuel concentration based on a linear length or thickness of the responsive material 220. If the linear length is shorter, the concentration of biofuel may be high, and if the linear length is longer, the concentration of biofuel may be low, similar to the gauge depicted in the illustrated embodiment of FIG. 1. A variety of sensor types may be utilized to determine a length of the responsive material, including optical sensors and linear or position transducers.

The actual range of linear movement of the responsive material 220 may be adjusted based on the initial size and dimensions of the responsive material 220. Additionally, the response time of the responsive material 220 may also vary based on the initial size and dimensions. These features may be varied as desired depending on the application.

In a further embodiment, the sensor 230 may measure electrical resistance of the responsive material 220 to determine a biofuel concentration. In this embodiment, the sensor 230 may include direct electrical connections to the responsive material 220 that enable the sensor 230 to measure a resistance or an electrical property of the responsive material 220. For example, the resistance of the responsive material 220 may be proportional to a dimensional property of the responsive material 220, which may enable the measuring device 200, by measuring the resistance, to determine biofuel content. Although described in connection with resistance, other electrical properties, such as impedance, may be indicative of dimensional properties of the responsive material 220, and may be measured to determine biofuel content. A variety of sensor-types may be utilized to measure an electrical property of the responsive material, including, for example, those used in conjunction with a rheostat.

In the illustrated embodiment of FIG. 3, the measuring device 200 is depicted in use with an control system 250, which is shown in phantom lines as an optional component. The control system 250 may be operably connected to the measuring device 200, and may be configured to obtain, from the measuring device 200, information relating to a biofuel content of a fuel blend in contact with the responsive material 220. The control system 250 may utilize this information as a basis for a variety of operations. In one embodiment, the control system 250 may be integrated into an engine control module (ECM) capable of controlling operation of an engine, such as the engine of a car. The control system 250 may operate the engine based on the biofuel content information obtained from the measuring device 200. In this embodiment, the measuring device 200 may be disposed within a fuel tank of the car so that the control system 250 can obtain biofuel content information about the fuel blend being supplied to the engine.

It should be understood that the measuring device 200 is not limited to use with a control system 250. For example, the measuring device 200 may operably connect to other circuitry, and may be capable of indicating biofuel content in a way other than through direct electrical contacts, such as by a visual indication or through wireless communication.

As discussed above, the dimensions and configuration of the responsive material 220 may vary from application to application, based on a variety of factors, including a desired response time. In embodiments in which the measuring device 200 is disposed within a fuel tank, the selected response time may be slower because the biofuel concentration may not change dramatically over time, unless the tank is filled. In other words, a fuel blend within the tank may not change dramatically until new fuel is introduced, and is diluted into the existing fuel, thereby potentially resulting in a different biofuel concentration.

The above description is that of current embodiments of the invention. Various alterations and changes can be made without departing from the spirit and broader aspects of the invention as defined in the appended claims, which are to be interpreted in accordance with the principles of patent law including the doctrine of equivalents. This disclosure is presented for illustrative purposes and should not be interpreted as an exhaustive description of all embodiments of the invention or to limit the scope of the claims to the specific elements illustrated or described in connection with these embodiments. For example, and without limitation, any individual element(s) of the described invention may be replaced by alternative elements that provide substantially similar functionality or otherwise provide adequate operation. This includes, for example, presently known alternative elements, such as those that might be currently known to one skilled in the art, and alternative elements that may be developed in the future, such as those that one skilled in the art might, upon development, recognize as an alternative. Further, the disclosed embodiments include a plurality of features that are described in concert and that might cooperatively provide a collection of benefits. The present invention is not limited to only those embodiments that include all of these features or that provide all of the stated benefits, except to the extent otherwise expressly set forth in the issued claims. Any reference to claim elements in the singular, for example, using the articles "a," "an," "the" or "said," is not to be construed as limiting the element to the singular. The technology disclosed and claimed herein may be available for licensing in specific fields of use by the assignee of record.

The embodiments of the invention in which an exclusive property or privilege is claims are defined as follows:

1. A measurement device for use in determining content of biofuel within a fuel blend, said measurement device comprising:
   a responsive material capable of changing dimensionally in response to changes in a concentration of biofuel within the fuel blend, wherein the fuel blend includes the biofuel and a petroleum-based fuel, wherein a dimensional property of said responsive material decreases in response to an increase in the concentration of the biofuel relative to the petroleum-based fuel, wherein the dimensional property of the responsive material increases in response to a decrease in the concentration of the biofuel relative to the petroleum-based fuel;
   an indicator that provides information relating to the concentration of biofuel based on one or more properties of said responsive material.

2. The measurement device as claimed in claim 1 wherein said responsive material is insoluble with respect to components of the fuel blend other than the biofuel.

3. The measurement device as claimed in claim 2 wherein said components include at least one of contaminants and additives.

4. The measurement device as claimed in claim 3 wherein said contaminants includes water.

5. The measurement device as claimed in claim 1 wherein said dimensional property includes at least one of thickness and volume, and wherein said one or more properties include at least one of thickness, volume, and an electrical impedance.

6. The measurement device as claimed in claim 1 wherein said indicator includes a gauge having a scale that indicates at least one of presence and concentration of biofuel based on linear dimension of said responsive material.

7. The measurement device as claimed in claim 1 wherein said indicator provides information relating to the concentration of biofuel based on a current state of said one or more properties of said responsive material and in response to exposure of said responsive material to the fuel blend.

8. The measurement device as claimed in claim 1 further comprising a sensor operably coupled to said indicator, wherein said indicator is an output of said sensor, and wherein said sensor is capable of measuring said one or more properties of said responsive material.

9. The measurement device as claimed in claim 8 wherein said sensor includes at least one of a linear transducer, an optical sensor, a strain gauge, a pressure sensor and a rheostat.

10. The measurement device as claimed in claim 1 wherein said responsive material is formed of silicone rubber.

11. A measurement device for use in determining content of biofuel within a fuel blend, said measurement device comprising:
- a responsive material having a solubility property with respect to the biofuel and other components of the fuel blend that results in one or more properties of said responsive material changing as the concentration of biofuel changes in the fuel blend, wherein the fuel blend includes the biofuel and a petroleum-based fuel, wherein a dimensional property of said responsive material decreases in response to an increase in the concentration of the biofuel relative to the petroleum-based fuel, wherein said dimensional property of said responsive material increases in response to a decrease in the concentration of the biofuel relative to the petroleum-based fuel; and
- an indicator that provides information relating to the concentration of biofuel as a function of said one or more properties of said responsive material.

12. The measurement device as claimed in claim 11 wherein said indicator identifies the concentration of biofuel based on said current state of said one or more properties.

13. The measurement device as claimed in claim 11 further comprising a sensor operably coupled to said indicator, said sensor capable of measuring said one or more properties of said responsive material, wherein said sensor determines a concentration of the biofuel based on said measured one or more properties, and provides said indicator information relating to said determined concentration.

14. The measurement device as claimed in claim 13 wherein said sensor includes at least one of a linear transducer, an optical sensor, a strain gauge, a pressure sensor, and a rheostat.

15. The measurement device as claimed in claim 14 wherein said sensor is a pressure sensor, wherein said responsive material is in a restricted space such that as the biofuel concentration changes, pressure within said restricted space changes, wherein said pressure sensor measures said pressure within said restricted space, and wherein said indicator indicates biofuel concentration based on said measured pressure.

16. The measurement device as claimed in claim 13 wherein said indicator is an output of said sensor.

17. The measurement device as claimed in claim 11 wherein said responsive material changes dimensionally as the concentration of biofuel changes in the fuel blend.

18. The measurement device as claimed in claim 11 wherein said indicator includes a scale capable of visually identifying at least one or presence and concentration of biofuel based on a dimensional property of said responsive material and in response to contact with the fuel blend.

19. The measurement device as claimed in claim 11 wherein said responsive material is soluble to biofuel and insoluble to at least one of contaminants and additives of the fuel blend.

20. The measurement device as claimed in claim 1 wherein the biofuel is ethanol, wherein the petroleum-based fuel is gasoline such that the fuel blend includes ethanol and the gasoline, and wherein said dimensional property of the responsive material decreases as an amount of the ethanol in the fuel blend increases relative to an amount of the gasoline.

* * * * *